US010993913B2

(12) United States Patent
Doi et al.

(10) Patent No.: US 10,993,913 B2
(45) Date of Patent: May 4, 2021

(54) STABLE OXALIPLATIN-ENCAPSULATING LIPOSOME AQUEOUS DISPERSION AND METHOD FOR STABILIZING SAME

(71) Applicants: Taiho Pharmaceutical Co., Ltd., Tokyo (JP); The University of Tokushima, Tokushima (JP)

(72) Inventors: Yusuke Doi, Tokushima (JP); Tatsuhiro Ishida, Tokushima (JP)

(73) Assignees: Taiho Pharmaceutical Co., Ltd, Tokyo (JP); University of Tokushima, Tokushima (JP)

( * ) Notice: Subject to any disclaimer, the term of this patent is extended or adjusted under 35 U.S.C. 154(b) by 0 days.

(21) Appl. No.: 16/502,798

(22) Filed: Jul. 3, 2019

(65) Prior Publication Data

US 2019/0321294 A1  Oct. 24, 2019

Related U.S. Application Data

(62) Division of application No. 14/420,544, filed as application No. PCT/JP2013/071720 on Aug. 9, 2013, now Pat. No. 10,383,822.

(30) Foreign Application Priority Data

Aug. 10, 2012 (JP) ................. 2012-178971

(51) Int. Cl.
| A61K 9/127 | (2006.01) |
| A61K 31/555 | (2006.01) |
| A61K 45/06 | (2006.01) |
| A61K 47/22 | (2006.01) |
| A61K 31/282 | (2006.01) |

(52) U.S. Cl.
CPC ............ *A61K 9/127* (2013.01); *A61K 31/282* (2013.01); *A61K 31/555* (2013.01); *A61K 45/06* (2013.01); *A61K 47/22* (2013.01)

(58) Field of Classification Search
None
See application file for complete search history.

(56) References Cited

U.S. PATENT DOCUMENTS

| 5,565,213 A | 10/1996 | Nakamori et al. |
| 5,716,988 A | 2/1998 | Ibrahim et al. |
| 5,776,488 A | 7/1998 | Mori |
| 6,045,821 A * | 4/2000 | Garrity ............... A61K 49/1812 424/1.21 |
| 2001/0006648 A1 | 7/2001 | Yamuchi et al. |
| 2002/0018224 A1 | 12/2002 | Yamauchi et al. |
| 2003/0224037 A1 | 12/2003 | Eriguchi et al. |
| 2004/0022842 A1 * | 2/2004 | Eriguchi ............... A61K 31/555 424/450 |
| 2007/0116753 A1 * | 5/2007 | Hong ................... A61K 31/337 424/450 |
| 2010/0330166 A1 * | 12/2010 | Ishida ................... A61K 9/127 424/450 |

FOREIGN PATENT DOCUMENTS

| CA | 2244213 A1 | 8/1997 |
| CN | 1628638 A | 6/2005 |
| JP | H054037 A | 1/1993 |
| JP | 2004010481 A | 1/2004 |
| JP | 2006248978 A | 9/2006 |
| JP | 2011521913 A | 7/2011 |
| WO | 9604904 A1 | 2/1996 |
| WO | 9728104 A2 | 8/1997 |
| WO | 9730696 A1 | 8/1997 |
| WO | 2006099169 A2 | 9/2006 |
| WO | 2007099377 A2 | 9/2007 |
| WO | 2008030818 A2 | 3/2008 |
| WO | 2009-528340 A | 8/2009 |
| WO | 2009096487 A1 | 8/2009 |
| WO | 2009141450 A | 11/2009 |

OTHER PUBLICATIONS

Genc et al., "Curvature-Tuned Preparation of Nanoliposmoes", Langmuir, 2009, vol. 25, No. 21, pp. 12604-12613.
Immordino et al., "Stealth liposomes: review of the basic science, rationale, and clinical applications, existing and potential", International Journal of Nanomedicine, 2006, vol. 1, No. 3, pp. 297-315.
Allen et al., "Drug Delivery Systems: Entering the Mainstream", Science, 2004, vol. 303, pp. 1818-1822.
Jiang et al., "In vitro and in vivo characterizations of PEGylated liposomal doxorubicin", Bioanalysis, 2011, vol. 3, No. 3, pp. 333-344.
Extended European Search Report for the corresponding EP Patent Application No. 13827386.7 dated Dec. 7, 2015.
Good et al., "Hydrogen Ion Buffers for Biological Research", Hydrogen Ion Buffers for Biological Research, vol. 5, No. 2, Feb. 1966, pp. 467-477.

* cited by examiner

*Primary Examiner* — Celeste A Roney
(74) *Attorney, Agent, or Firm* — Rothwell, Figg, Ersnt & Manbeck, P.C.

(57) ABSTRACT

An object of the present invention is to provide an oxaliplatin-encapsulating liposome aqueous dispersion that has excellent long-term storage stability. The present invention provides an aqueous dispersion of liposomes encapsulating oxaliplatin, the oxaliplatin-encapsulating liposome aqueous dispersion containing 2-morpholinoethanesulfonic acid in an external aqueous phase.

14 Claims, 1 Drawing Sheet

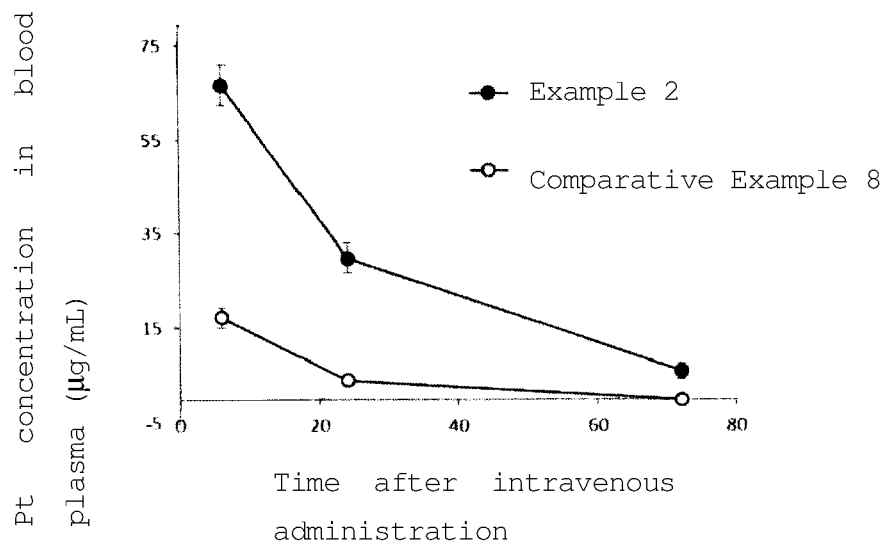

STABLE OXALIPLATIN-ENCAPSULATING LIPOSOME AQUEOUS DISPERSION AND METHOD FOR STABILIZING SAME

CROSS REFERENCE TO RELATED APPLICATION

This application is divisional of U.S. Ser. No. 14/420,544 filed Feb. 9, 2015, which is a is a 35 U.S.C. 371 National Phase Entry Application from PCT/JP2013/071720, filed Aug. 9, 2013, which claims the benefit of priority from Japanese Patent Application No. 2012-178971, filed Aug. 10, 2012 (the entirety thereof is incorporated herein by reference). The present invention relates to a technique that enables long-term storage of oxaliplatin-encapsulating liposomes in the form of an aqueous solution.

TECHNICAL FIELD

Background Art

With recent developments in nanotechnology, attempts have been made to apply nanotechnology to pharmaceutical products. In one such attempt, liposomes are formed by dispersing phospholipids in water. The liposome is a closed endoplasmic reticulum formed of a bilayer membrane with hydrophobic groups of phospholipids facing each other. Liposomes are composed of the same components as biological membranes, and are therefore highly biocompatible. Further, many studies have been conducted on liposomes as drug carriers that can carry either hydrophilic drugs or hydrophobic drugs, because hydrophilic drugs can be contained in the endoplasmic reticulum, whereas hydrophobic drugs can be embedded in the liposome membrane (Non-patent Literature (NPL) 1 and 2). Characteristics of liposomes, such as circulation in blood and transport into tumors, depend on the physical properties (e.g., particle size, surface charge, and drug release rate) of liposomes. To maintain these physical properties, the chemical stability of phospholipids, which are a main component of the liposome membrane, is important. Degradation of phospholipids reduces the stability of liposomes in the living body, and causes pharmacokinetic changes in the body. Pharmacokinetic changes in the body directly cause reduction of pharmacological effects, generation of unexpected side effects, etc. Therefore, protection of phospholipids is considered to be essential for application of liposomes to pharmaceutical products.

Oxaliplatin is a platinum complex compound synthesized by Dr. Kidani et al. in 1978. Oxaliplatin is one of the most widely used anticancer agents worldwide in the treatment of colorectal cancer. However, oxaliplatin, which has a high rate of binding to plasma proteins and hemocytes, and which is prone to distribution in normal tissues, has been confirmed to have high toxicity, such as peripheral neurotoxicity. This is similar to other anticancer agents, and thus needs to be improved. The application of a liposome technique has been studied as an approach for this improvement (see Patent Literature (PTL) 1 to 3). The liposome technique, which is expected to inhibit non-selective systemic distribution and promote transport into tumors due to the enhanced permeability and retention effect (EPR effect), can be expected to provide higher antitumor activity while reducing the toxicity of oxaliplatin. PTL 1 discloses a liposome preparation obtained by encapsulating oxaliplatin in liposomes modified with PEG (polyethylene glycol), which has long circulation in blood. PTL 2 discloses a PEG-modified liposome preparation further modified with transferrin. PTL 3 discloses a method for efficiently encapsulating oxaliplatin, and liposomal effects thereof. However, oxaliplatin has poor compatibility with other additives (PTL 4). Further, reduction of pH due to a degradation product is considered to cause rupture of liposomes. However, none of the above prior art documents disclose a method for long-term stabilization of liposome preparations that are indispensable as pharmaceutical products.

Known techniques for stabilizing liposome aqueous dispersions include, for example, the use of a buffer solution of citric acid or tartaric acid (PTL 5), histidine (NPL 3), taurine (PTL 6), or tris (PTL 7) as a stabilizer. However, these documents are silent as to whether the techniques disclosed therein can be used for stabilization of an oxaliplatin-encapsulating liposome aqueous dispersion. These stabilizers are mainly added to reduce hydrolysis of phospholipids due to pH change, and are not additives used in consideration of compatibility with a specific compound. Accordingly, depending on the type of drug to be encapsulated, contact of the drug with an additive may affect the stability of the drug and reduce the quality as a pharmaceutical product. In the case of liposomal formulations, pH reduction in aqueous dispersions accelerates hydrolysis of phospholipids. In oxaliplatin-encapsulating liposome aqueous dispersions, oxaliplatin that exists in a very low concentration in the external aqueous phase is prone to decompose, and desorption of oxalic acid causes pH reduction (PTL 4 discloses that oxaliplatin having a concentration of less than 1 mg/mL tends to be unstable). In addition, release of carboxylic acid as a hydrolyzate of phospholipids further reduces pH reduction in the system. The pH reduction due to oxalic acid and/or carboxylic acid is considered to accelerate degradation of phospholipids and further reduce pH, thus resulting in a negative cycle. In fact, during research, the present inventors produced oxaliplatin-encapsulating liposome preparations by using aqueous dispersions prepared with reference to the above prior art documents, and confirmed accelerated degradation of oxaliplatin or phospholipids over time.

CITATION LIST

Patent Literature

PTL 1: WO2009/096487
PTL 2: JP2004-10481A
PTL 3: WO2007/099377
PTL 4: WO1996/04904
PTL 5: WO1997/30696
PTL 6: JPH05-004037A
PTL 7: WO1997/28104

Non-Patent Literature

NPL 1: International Journal of Nanomedicine, 2006, 1 (3), 297-315
NPL 2: Science, (2004), Vol. 303, 1818-1822
NPL 3: Bioanalysis, (2011), 3 (3), 333-344

SUMMARY OF INVENTION

Technical Problem

An object of the present invention is to provide an oxaliplatin-encapsulating liposome aqueous dispersion that has high long-term storage stability. Further, the present invention provides a technique of stabilizing an oxaliplatin-encapsulating liposome aqueous dispersion.

Solution to Problem

The present inventors conducted extensive research and, as a result, found that when 2-morpholinoethanesulfonic acid (hereinafter referred to as MES) is contained as a stabilizer in the external aqueous phase of liposomes, an aqueous dispersion in which phospholipids are sufficiently stably maintained for a long period of time can be provided while the total oxaliplatin content of liposomes is hardly affected. The inventors further found that addition of MES only to the external aqueous phase of liposomes can stabilize an oxaliplatin-encapsulating liposome aqueous dispersion for a long period of time. The inventors further investigated the optimum pH, etc., of the liposome aqueous dispersion, and accomplished the present invention.

Specifically, the present invention provides the following liposome aqueous dispersions, stabilizer for the dispersions, and methods for stabilizing the dispersions.

Item 1. An oxaliplatin-encapsulating liposome aqueous dispersion comprising an external aqueous phase that contains 2-morpholinoethanesulfonic acid.

Item 2. The oxaliplatin-encapsulating liposome aqueous dispersion according to Item 1, wherein the dispersion comprises an internal aqueous phase that substantially contains no 2-morpholinoethanesulfonic acid.

Item 3. The oxaliplatin-encapsulating liposome aqueous dispersion according to Item 1 or 2, wherein the dispersion has a pH of 5 to 8.

Item 4. The oxaliplatin-encapsulating liposome aqueous dispersion according to any one of Items 1 to 3, wherein the liposomes comprise at least one saturated phospholipid as a liposome component.

Item 5. The oxaliplatin-encapsulating liposome aqueous dispersion according to any one of Items 1 to 4, wherein the liposomes comprise as a liposome component at least one saturated phospholipid selected from the group consisting of hydrogenated purified soybean phosphatidylcholines, distearoylphosphatidylcholines, dipalmitoylphosphatidylcholines, and hydrogenated purified egg yolk phosphatidylcholines.

Item 6. The oxaliplatin-encapsulating liposome aqueous dispersion according to any one of Items 1 to 5, wherein the amount of 2-morpholinoethanesulfonic acid is 0.00001 to 10 parts by mass (preferably 0.00005 to 1 part by mass, and more preferably 0.0001 to 0.1 parts by mass) per part by mass of liposome-forming phospholipid.

Item 7. A stabilizer for an oxaliplatin-encapsulating liposome aqueous dispersion containing 2-morpholinoethanesulfonic acid or a salt thereof as an active ingredient.

Item 8. A method for stabilizing an oxaliplatin-encapsulating liposome aqueous dispersion, comprising adding 2-morpholinoethanesulfonic acid or a salt thereof to the oxaliplatin-encapsulating liposome aqueous dispersion.

Item 9. An antitumor agent comprising the oxaliplatin-encapsulating liposome aqueous dispersion according to any one of Items 1 to 6.

Item 10. A method for treating a cancer, comprising administering the oxaliplatin-encapsulating liposome aqueous dispersion according to any one of Items 1 to 6 to a mammal.

Item 11. Use of the oxaliplatin-encapsulating liposome aqueous dispersion according to any one of Items 1 to 6 in the preparation of an antitumor agent.

Item 12. The oxaliplatin-encapsulating liposome aqueous dispersion according to any one of Items 1 to 6, which is for use in the treatment of a cancer.

Item 13. An antitumor effect potentiator for enhancing antitumor activity of an antitumor agent, the potentiator comprising the oxaliplatin-encapsulating liposome aqueous dispersion according to any one of Items 1 to 6.

Item 14. The method for treating a cancer according to Item 10, further comprising administering an antitumor agent to a mammal.

Item 15. Use of the oxaliplatin-encapsulating liposome aqueous dispersion according to any one of Items 1 to 6 in the preparation of a potentiator for enhancing an effect of an antitumor agent.

Item 16. The oxaliplatin-encapsulating liposome aqueous dispersion according to any one of Items 1 to 6, which is for enhancing an effect of an antitumor agent.

Advantageous Effects of Invention

According to the present invention, an oxaliplatin-encapsulating liposome aqueous dispersion having excellent long-term storage stability can be provided. The present invention enables the provision of an oxaliplatin-encapsulating liposome aqueous dispersion that is stable for a long period of time, even when stored at a relatively high temperature of 40° C.

BRIEF DESCRIPTION OF DRAWINGS

FIG. 1 shows changes in Pt concentration in blood plasma over time in Test Example 3.

DESCRIPTION OF EMBODIMENTS

The MES used in the present invention is a known compound, and is available as 2-morpholinoethanesulfonic acid from manufacturers such as Sigma-Aldrich (product code: M8250), Merck (product code: 106126), and Dojindo Laboratories, Inc. (product code: GB81). In the present invention, the salt of MES refers to a salt commonly used in the field of organic chemistry. For example, since MES has a sulfonic acid group, a base addition salt formed by adding a base to the sulfonic acid group can be used.

Examples of the base addition salt include alkali metal salts such as sodium salts and potassium salts; alkaline earth metal salts such as calcium salts and magnesium salts; ammonium salts; and organic amine salts such as trimethylamine salts, triethylamine salts, dicyclohexylamine salts, ethanolamine salts, diethanolamine salts, triethanolamine salts, procaine salts, and N,N'-dibenzylethylenediamine salts.

The amount of MES or a salt thereof to be added, based on parts by mass of MES, is 0.00001 to 10 parts by mass, preferably 0.00005 to 1 part by mass, and more preferably 0.0001 to 0.1 parts by mass, per part by mass of the liposome-forming phospholipid(s).

In the present invention, MES or a salt thereof may be added in the form of a solution or powder to the external aqueous phase of the liposome aqueous dispersion during the liposome manufacturing process, or may be added by replacing the external aqueous phase with a buffer containing a prescribed concentration of MES by ultrafiltration, dialysis, or the like. The addition may be performed concurrently with an unencapsulated drug removal step. Alternatively, it is also possible to add MES or a salt thereof to a final aqueous dispersion. Adding a predetermined amount of a concentrated MES solution (the volume to be added is 1% or less of the drug) immediately before filter sterilization is preferable. Adding MES or a salt thereof to the final aqueous dispersion also results in substantial presence of MES or a salt thereof in the external aqueous phase.

In the present invention, the external aqueous phase preferably has a pH of 5.0 to 8.0, more preferably 5.5 to 7.5, and even more preferably 6.0 to 7.0. In the present invention, the pH of the external aqueous phase is determined by dipping electrodes of a pH meter into the liposome dispersion. The pH of the external aqueous phase may be adjusted to a desired pH value, for example, by adding a pH adjuster after adding MES or a salt thereof to the oxaliplatin-encapsulating liposome aqueous dispersion. Examples of pH adjusters usable for this pH adjustment include alkali metal hydroxides and/or alkali earth metal hydroxides. Specific examples include sodium hydroxide, potassium hydroxide, and sodium hydrogen carbonate. Sodium hydroxide is preferable.

In the present invention, "long-term storage stability" means that none of precipitation, aggregation, and particle size change occur after storage in a cold place for at least 6 months, and that there is little degradation of oxaliplatin and phospholipids, or that degradation occurs at an acceptable level.

In the present invention, "encapsulating" refers to the state in which a drug (oxaliplatin) is encapsulated in the closed space of a liposome formed of a lipid membrane, or to the state in which a drug (oxaliplatin) is carried in such a manner that a portion or all of the drug is contained within the lipid layers forming the membrane.

The "oxaliplatin" (hereinafter sometimes referred to as "L-OHP") used in the present invention is a known compound and is represented by cis-oxalato(1R,2R-diaminocyclohexane)platinum(II). Binding of L-OHP to DNA of cancer cells causes functional damage of the DNA and DNA strand cleavage, leading to death of the cancer cells. Oxaliplatin may be produced by using a known method, such as the methods disclosed in JPS60-41077B and JPH06-211833A.

The "liposome" to be used in the present invention is a closed vesicle having an internal aqueous phase portion enclosed by a lipid bilayer membrane that is formed by dispersing in water at least one phospholipid that is a cell membrane component. Liposomes can be classified into the following three types according to the particle size and the number of lipid bimolecules: multilamellar vesicles (MLV), large unilamellar vesicles (LUV), and small unilamellar vesicles (SUV). As long as the liposome is a closed vesicle having a lipid bilayer structure, any type of liposome can be used in the present invention.

The liposomes used in the present invention should form a stable liposome structure before and after the administration to living organisms. Examples of phospholipids that form the liposomes include saturated phospholipids, which can be selected, for example, from hydrogenated purified egg yolk phosphatidylcholines (phase transition temperature: 50° C., hereinafter referred to as HEPC), hydrogenated purified soybean phosphatidylcholines (phase transition temperature: about 55° C., hereinafter referred to as HSPC), dipalmitoylphosphatidylcholines (phase transition temperature: about 41° C., hereinafter referred to as DPPC), and distearoylphosphatidylcholines (phase transition temperature: about 58° C., hereinafter referred to as DSPC). Among these, HSPC is more preferable. By using phospholipids having different phase transition temperatures, the fluidity of the bimolecular lipid membrane of liposomes can be changed. The most suitable phospholipid can be selected in view of the drug encapsulation rate, stability in a pharmaceutical preparation, in vivo pharmacokinetic changes after administration, etc.

In this specification, "hydrogenated egg yolk phosphatidylcholines" refer to those obtained by hydrogenating phosphatidylcholines derived from egg yolk. Examples of preferable hydrogenated egg yolk phosphatidylcholines include those comprising as a main component a phosphatidylcholine in which the acyl moiety is an acyl group derived from a $C_{16-18}$ saturated straight-chain fatty acid. In the present invention, "hydrogenated purified egg yolk phosphatidylcholines" refer to those obtained by purifying hydrogenated egg yolk phosphatidylcholines. For example, hydrogenated egg yolk phosphatidylcholines having a purity of 80% or more, and preferably 90% or more, can be used.

In this specification, "hydrogenated soybean phosphatidylcholines" refer to those obtained by hydrogenating phosphatidylcholines derived from soybean. Examples of preferable hydrogenated soybean phosphatidylcholines include those comprising, as a main component, a phosphatidylcholine in which the acyl moiety is an acyl group derived from a $C_{16-18}$ saturated straight-chain fatty acid. In the present invention, "hydrogenated purified soybean phosphatidylcholines" refer to those obtained by purifying hydrogenated soybean phosphatidylcholines. For example, hydrogenated soybean phosphatidylcholines having a purity of 80% or more, preferably 90% or more, can be used.

To physically or chemically stabilize the lipid bilayer and to adjust the membrane fluidity, the lipid bilayer may comprise, for example, cholesterol, cholesterol succinic acid, lanosterol, dihydrolanosterol, desmosterol, dihydrocholesterol, and like animal-derived sterols; stigmasterol, sitosterol, campesterol, brassicasterol, and like plant-derived sterols (phytosterols); zymosterol, ergosterol, and like microorganism-derived sterols; glycerol, sucrose, and like saccharides; triolein, trioctanoin, and like glycerine fatty acid esters. These may be used singly, or in a combination of two or more. The amount thereof is not particularly limited, but is preferably 10 to 50% (molar ratio), and more preferably 20 to 40% (molar ratio), based on the total amount of the lipids forming the lipid bilayer.

The lipid bilayer may comprise tocopherol, propyl gallate, ascorbyl palmitate, butylated hydroxytoluene, and like antioxidant agents; stearylamine, oleylamine, and like charged materials for providing a positive charge; dicetyl phosphate and like charged materials for providing a negative charge; and membrane extrinsic protein, membrane intrinsic protein, and like membrane proteins. The amount thereof can be suitably adjusted.

Further modifying the liposome membrane surface with a ligand as desired can further improve liposomal stability in blood, tissue distribution, and transport into tumor tissues. Examples of such ligands include hydrophilic polymers such as polyethylene glycol and polyglycerin, lipids that contain a basic functional group such as an amino group, an amidino group, or a guadinino group (hereinafter referred to as "cationized lipids"), peptides, lectins, antibodies, saccharides, glycoproteins, and glycolipids.

In the present invention, the "polyethylene glycol" includes not only unsubstituted polyethylene glycol, but also polyethylene glycol derivatives having a covalently bonded oleophilic (hydrophobic) side chain. Specific examples of the oleophilic side chain include alkyl chains, phospholipids, and cholesterols. Phospholipids having a covalently bonded polyethylene glycol are preferable. Examples of phospholipids having a covalently bonded polyethylene glycol include EPC (egg phosphatidylcholine), DLPC (dilinoleoylphosphatidylcholine), DMPC (dimyristoylphosphatidylcholine), DPPC (dipalmitoylphosphatidylcholine), DSPC (distearoylphosphatidylcholine), POPC (palmitoyloleoylphosphatidylcholine), DOPC (dioleoylphosphatidylcholine), DSPE (1,2-distearoyl-sn-glycero-3-phosphoethanolamine), DOPE (dioleoylphosphatidylethanolamine), and SOPE (stearyloleoylphosphatidylcholine). Among these, EPC, DOPC, DSPE, DOPE, SOPE, and the like are preferable, and DSPE is more preferable. A wide variety of polyethylene glycol derivatives that are usually used to improve the stability of liposomes can be used as the polyethylene glycol derivatives. Similarly, in the present invention, the "polyglycerin" includes not only unsubstituted polyglycerin, but also polyglycerin derivatives having a covalently bonded oleophilic (hydrophobic) side chain. Specific examples of the oleophilic side chain include alkyl chains, phospholipids, and cholesterols. A wide variety of polyglycerin derivatives that are usually used to improve the stability of liposomes can be used as the polyglycerin derivatives. If necessary, the aqueous phase used as a basis may further contain isotonizing agents (e.g., mannitol, glycerol, sucrose, glucose, and sodium chloride) and preservatives (e.g., parabens, chlorobutanol, benzyl alcohol, and propylene glycol), as long as the effects of the present invention are not impaired. Oxaliplatin is in the form of a solution in this aqueous phase and is present in the liposomes, whereas MES, which is a stabilizer, is in the form of a solution in an aqueous phase and is present outside the liposomes.

Further, a small amount of taurine may be added outside the liposomes in order to assist the liposome-stabilizing action of MES. The amount of taurine added is not more than 1 part by mass, preferably 0.0001 to 0.5 parts by mass, per part by mass of MES.

The liposome preparation of the present invention is prepared by using a known method. Examples of the known method for preparing a liposome preparation include a reverse phase evaporation method (Proc. Natl. Acad. Sci. USA, Vol. 75-4194, 1978, WO97/48398), a freezing and thawing method (Arch. Biochem. Biophys. Vol. 212, 186, 1981), a pH gradient method (Biochem. Biophys. Acta, Vol. 816, 294, 1985, JPH7-165560A), and a hydration method.

Among these methods, when the reverse phase evaporation method is used, the liposome preparation of the present invention can be produced, for example, by the following process. A lipid component is dissolved in a solvent such as chloroform, ether, or ethanol, and the resulting solution is placed in a recovery flask. The solvent is distilled off under reduced pressure to form a lipid thin film. Subsequently, a mixed liquid containing chloroform and diethyl ether at a chloroform/diethyl ether ratio of 1/2 is added to dissolve the thin film. An aqueous oxaliplatin solution is added thereto, and the mixture is sonicated at 25° C. for 15 minutes to obtain an emulsion. Subsequently, the organic solvent portion is removed by distillation under reduced pressure using an evaporator for about 1 hour while vortexing to invert a w/o emulsion to an o/w emulsion. Liposomes are thus formed, and oxaliplatin is simultaneously encapsulated in the liposomes.

An example of production of liposomes using a hydration method is described below. After one or more lipid components, such as phospholipids, cholesterols, and high-molecular-weight derivatives, are dissolved in an organic solvent, the organic solvent is removed by evaporation to obtain a lipid membrane. Examples of the organic solvent used in this process include hydrocarbons such as pentane, hexane, heptane, and cyclohexane; halogenated hydrocarbons such as methylene chloride and chloroform; aromatic hydrocarbons such as benzene and toluene; lower alcohols such as methanol and ethanol; esters such as methyl acetate and ethyl acetate; and ketones such as acetone. These may be used singly, or in a combination of two or more.

After one or more lipids that are a component of the lipid bilayer are dissolved in an organic solvent, the organic solvent is removed by evaporation to obtain a lipid membrane. Subsequently, the lipid membrane is hydrated with an oxaliplatin aqueous solution, and stirred or ultrasonicated to produce liposomes.

Alternatively, the liposome preparation of the present invention can also be produced in accordance with the following production example. One or more liposome membrane-forming lipids (e.g., phospholipids, cholesterols, and hydrophilic polymer derivatives) are dissolved in a volatile organic solvent, preferably absolute ethanol, while warming to obtain a lipid solution. The warming temperature should be set to not lower than the phase transition temperature of the phospholipids used. When HSPC is used, the warming temperature is 50 to 80° C., and is preferably 60 to 70° C. Subsequently, an osmotic modulating agent, a pH adjuster, oxaliplatin, etc., are dissolved in water. After the resulting solution is warmed to a temperature similar to the lipid solution temperature, the solution is mixed with the lipid solution, and stirred to obtain a crude liposome dispersion. Stirring may be performed by using a magnetic stirrer, a propeller-style agitator, or the like. Further, the dispersion may be emulsified by using a homomixer or the like, if necessary.

The liposome composition used in the present invention preferably comprises a phospholipid (e.g., HEPC, HSPC, DPPC, or DSPC, and more preferably HSPC), cholesterol, and polyethylene glycol-linked phospholipid (e.g., polyethylene glycol-linked DSPE). Specifically, the liposome composition ratio (on a molar basis) is preferably such that the ratio of phospholipid:cholesterol:phospholipid having a covalently bonded polyethylene glycol is preferably 1:0.01 to 2:0.005 to 0.5, and more preferably 1:0.1 to 1:0.01 to 0.1.

It has been reported that the particle size of liposomes strongly affects biodistribution of encapsulated oxaliplatin and transport into tumor tissues (Biol. Pharm. Bull., Vol. 17, 935, 1994). To obtain appropriately and uniformly sized liposomes containing oxaliplatin therein, particle sizing is preferably performed in the present invention. For example, supersonic treatment using a biodisruptor (produced by Nippon Seiki Co., Ltd., etc.) or high-pressure emulsification using a nanomizer (produced by Yoshida Kikai Co., Ltd.) may be performed to adjust the particle size of liposomes to a mean particle size of about 100 to 200 nm. Alternatively, the liposome solution may be subjected to sizing (0.4 μm, 0.2 μm, 0.1 μm, and 0.08 μm) under a pressure of nitrogen using various polycarbonate membrane filters to adjust the mean particle size to about 100 to 300 nm.

The term "mean particle size" as used herein refers to an average particle diameter determined by a dynamic light-scattering method using FPAR-1000 (produced by Otsuka Electronics Co., Ltd.).

The liposome preparation according to the present invention can be obtained, for example, by methods described in WO2009/096487, JP2004-10481A, WO2007/099377, and JP2006-248978A that disclose oxaliplatin-encapsulating liposome preparations.

In a preferable embodiment, the liposome preparation of the present invention is produced by using an oxaliplatin solution prepared by dissolving oxaliplatin in a 1 to 20% sucrose solution at a concentration of 1 to 20 mg/mL. The oxaliplatin-encapsulating liposome preparation thus obtained is subjected to, if necessary, ultracentrifugation, gel filtration, ultrafiltration, or dialysis, which may be conducted singly or in a suitable combination, to thereby remove oxaliplatin not encapsulated in the liposome.

The oxaliplatin-encapsulating liposome preparation obtained by the aforementioned method can be used unmodified as an aqueous dispersion. However, in view of storage period length, storage conditions, etc., the oxaliplatin-encapsulating liposome preparation may be freeze-dried and stored after adding an excipient, such as mannitol, trehalose, lactose, or glycine, and the resulting product may be used as the MES-containing aqueous dispersion of the present invention. Alternatively, the oxaliplatin-encapsulating liposome preparation may be cryopreserved after adding a cryopreservation agent, such as glycerol, and the resulting product may be used as the MES-containing aqueous dispersion of the present invention.

In a preferable embodiment, the oxaliplatin-encapsulating liposome preparation contains oxaliplatin in an amount of 1 to 100 µg/mg of phospholipids, preferably 5 to 60 µg/mg of phospholipids, and more preferably 10 to 50 µg/mg of phospholipids.

The oxaliplatin-encapsulating liposome preparation of the present invention has a mean particle diameter of preferably 50 to 300 nm, more preferably 80 to 200 nm, and even more preferably 100 to 150 nm.

The liposome dispersion of the present invention may be used both in vivo and in vitro. When the liposome dispersion of the present invention is used in vivo, the administration route may be, for example, intravenous injection or intravenous drip. The dosage and administration frequency can be suitably adjusted according to the amount of oxaliplatin encapsulated in the liposome dispersion of the present invention, the patient, etc.

A feature of the oxaliplatin-encapsulating liposome aqueous dispersion of the present invention is that oxaliplatin is contained in the internal aqueous phase of liposomes. The oxaliplatin-encapsulating liposome aqueous dispersion of the present invention includes, as long as the effects of the present invention are maintained, those in which a portion of oxaliplatin permeates the lipid bilayer and leaks out to the outer aqueous phase. Similarly, the oxaliplatin-encapsulating liposome aqueous dispersion of the present invention further includes, as long as the effects of the present invention are maintained, those in which a portion of MES present in the external aqueous phase penetrates into the internal aqueous phase.

The oxaliplatin-encapsulating liposome aqueous dispersion is generally suspended or diluted with a physiologically acceptable aqueous solution, and used as an injectable preparation (intravenously, intraperitoneally, intramuscularly, or subcutaneously administered preparation). However, the oxaliplatin-encapsulating liposome aqueous dispersion may also be processed and used as an oral preparation, an ophthalmic solution, a nasal spray, an inhalant, a suppository, a transdermal preparation, a transmucosal preparation, etc. In this case, the oxaliplatin-encapsulating liposome aqueous dispersion is formed into a pharmaceutical composition in a usual manner using one or more suitable pharmaceutical carriers. Examples of usable carriers include those that are commonly used in conventional pharmaceutical preparations. Specific examples thereof include isotonizing agents, pH adjusters, preservatives, stabilizers, colorants, corrigents, odor-masking agents, and surfactants. These carriers can be used as long as the effects of the present invention are not impaired.

There is no particular limitation on the type of malignant tumor to be treated by administering the pharmaceutical preparation of the present invention. Examples of the malignant tumor include epithelial cancers (e.g., respiratory cancers, digestive system cancers, reproductive system cancers, and endocrine system cancers), sarcomas, and hematopoietic cell tumors, preferably epithelial cancers, and more preferably digestive system cancers. There is no particular limitation on the type of organ where the tumor originates. Specific examples include lung cancer, gastric cancer, colon cancer, rectal cancer, esophageal cancer, breast cancer, head and neck cancer, liver cancer, gallbladder/bile duct cancer, pancreatic cancer, uterine cancer, uterine cervical cancer, ovarian cancer, renal cancer, bladder cancer, prostate cancer, pharyngeal cancer, brain tumor, leukemia, melanoma, and malignant lymphoma. In particular, a combination of the pharmaceutical preparation with a 5-FU-based anticancer agent is expected to provide a remarkable effect on colon cancer, rectal cancer, gastric cancer, esophageal cancer, breast cancer, and head and neck cancer. Further, a remarkable effect can also be expected on typical drug-resistant tumors and tumors that are developing drug resistance.

The amount of oxaliplatin to be contained in such a dosage unit form varies depending on the condition of the patient to whom the preparation is administered, or on the dosage form. The desirable amount of oxaliplatin per unit dosage form is typically about 0.05 to 1,000 mg for oral preparations, about 0.01 to 500 mg for injections, and about 1 to 1,000 mg for suppositories.

The daily dose of the drug in such a dosage form varies depending on the condition, body weight, age, sex, etc., of the patient, and cannot be generalized. The daily dose for adults (body weight: 50 kg) may be typically about 0.05 to 5,000 mg, preferably 0.1 to 1,000 mg, which is preferably administered once or in about two or three divided portions per day.

Examples of mammals to which the oxaliplatin-encapsulating liposome aqueous dispersion of the present invention is administered include humans, monkeys, mice, rats, rabbits, dogs, cats, cows, horses, pigs, and sheep. The oxaliplatin-encapsulating liposome aqueous dispersion of the present invention has an effect of enhancing the antitumor activity of antitumor agents. Accordingly, the oxaliplatin-encapsulating liposome aqueous dispersion of the present invention can be used as an antitumor effect potentiator for enhancing the antitumor activity of an antitumor agent.

A wide variety of known antitumor agents can be used as the antitumor agent to be used in combination with the oxaliplatin-encapsulating liposome aqueous dispersion of the present invention. Examples of such antitumor agents include 5-fluorouracil, doxifluridine, capecitabine, a combination anticancer drug that contains three components, i.e., tegafur, gimeracil, and oteracil potassium, as active ingredients, and CPT-11.

The antitumor effect potentiator of the present invention may be administered separately or concurrently with an antitumor agent. More specifically, the antitumor effect potentiator of the present invention may be administered concurrently or at any time before or after the administration of the antitumor agent used in combination therewith. Preferably, the antitumor effect potentiator is administered concurrently or within 4 hours before or after the administration of the antitumor agent, and more preferably within 2 hours before or after the administration of the antitumor agent.

When the antitumor effect potentiator is administered concurrently with or separately from the antitumor agent, the antitumor effect potentiator is preferably administered in an amount such that the amount of oxaliplatin per mole of the antitumor agent is within the range of about 0.1 to 5 moles, preferably about 0.1 to 3 moles, and more preferably about 0.2 to 2 moles.

EXAMPLES

Production Examples, Reference Examples, Examples, Comparative Examples, and Test Examples are given below to illustrate the invention in more detail; however, the scope of the invention is not limited by these Examples and Test Examples.

Example 1

(1) Preparation of the MES Solution

A 3 mM aqueous solution of 2-morpholinoethanesulfonic acid (produced by Dojindo Laboratories Co., Ltd., product code: 349-01623) (hereinafter referred to as "MES solution") was prepared and adjusted to a pH of 6.0 to 6.5 with 0.1 N NaOH.

(2) Preparation of Samples for Assessing Compatibility 1.12 g of a mixed lipid powder (HSPC/Chol/mPEG2000-DSPE=2/1/0.1, mol/mol) was added with stirring to 50 mL of a 10% sucrose solution warmed to 60 to 70° C. A more homogeneously emulsified state was then created by using a homomixer or the like as appropriate. Subsequently, the emulsion was passed through a polycarbonate filter with a pore diameter of 0.2 μm several times to obtain a dispersion of placebo liposomes with a mean particle size of 100 to 200 nm. This dispersion was used as an HSPC specimen.

The MES solution prepared above in (1) was added to 1 mL of an oxaliplatin specimen (1 mg/mL aqueous solution) to make the total volume 20 mL. The resulting mixture was used as a sample for assessing the compatibility of oxaliplatin with MES. Similarly, the MES solution was added to 1 mL of the HSPC specimen to make the total volume 20 mL. The resulting mixture was used as a sample for assessing the compatibility of HSPC with MES.

Comparative Example 1

A 10% sucrose solution was added to 1 mL of the oxaliplatin specimen and to 1 mL of the HSPC specimen in the same manner as in Example 1 to make the total volume of each mixture 20 mL. Each mixture was used as a sample for assessing stability of stabilizer-free oxaliplatin or stabilizer-free HSPC.

Comparative Example 2

A 3 mM citrate buffer with a pH of 6.0 to 6.5 was prepared. This citrate buffer was added to 1 mL of the oxaliplatin specimen and to 1 mL of the HSPC specimen in the same manner as in Example 1 to make the total volume of each mixture 20 mL. Each mixture was used as a sample for assessing the compatibility of oxaliplatin or HSPC with citric acid.

Comparative Example 3

A 3 mM tartaric acid buffer with a pH of 6.0 to 6.5 was prepared. This tartaric acid buffer was added to 1 mL of the oxaliplatin specimen and to 1 mL of the HSPC specimen in the same manner as in Example 1 to make the total volume of each mixture 20 mL. Each mixture was used as a sample for assessing the compatibility of oxaliplatin or HSPC with tartaric acid.

Comparative Example 4

A 3 mM histidine aqueous solution with a pH of 6.0 to 6.5 was prepared. This histidine aqueous solution was added to 1 mL of the oxaliplatin specimen and to 1 mL of the HSPC specimen in the same manner as in Example 1 to make the total volume of each mixture 20 mL. Each mixture was used as a sample for assessing the compatibility of oxaliplatin or HSPC with histidine.

Comparative Example 5

A 3 mM taurine aqueous solution with a pH of 6.0 to 6.5 was prepared. This taurine aqueous solution was added to 1 mL of the oxaliplatin specimen and to 1 mL of the HSPC specimen to make the total volume of each mixture 20 mL. Each mixture was used as a sample for assessing the compatibility of oxaliplatin or HSPC with taurine.

Comparative Example 6

A 3 mM Tris aqueous solution with a pH of 6.0 to 6.5 was prepared. This Tris aqueous solution was added to 1 mL of the oxaliplatin specimen and to 1 mL of the HSPC specimen in the same manner as in Example 1 to make the total volume of each mixture 20 mL. Each mixture was used as a sample for assessing the compatibility of oxaliplatin or HSPC with Tris.

Comparative Example 7

A 3 mM HEPES aqueous solution with a pH of 6.0 to 6.5 was prepared. This HEPES aqueous solution was added to 1 mL of the oxaliplatin specimen and to 1 mL of the HSPC specimen in the same manner as in Example 1 to make the total volume of each mixture 20 mL. Each mixture was used as a sample for assessing the compatibility of oxaliplatin or HSPC with HEPES.

Test Example 1 Assessment of Compatibility of Oxaliplatin and HSPC with Various Additives (Stability Test)

The samples obtained in Example 1 to Comparative Example 7 were placed in vials, which were sealed tightly. Thereafter, the oxaliplatin-containing samples were stored at 60° C., whereas the HSPC-containing samples were stored at 40° C. The concentrations of oxaliplatin and HSPC in the samples were determined by HPLC, and the compatibility was assessed by comparing the initial values and the values after 10 days of storage. Table 1 shows the percentages of oxaliplatin and HSPC concentrations after 10 days of storage relative to the initial concentrations.

TABLE 1

Assessment of compatibility of the oxaliplatin solution and placebo liposomes with various additives

| Percentage of the content after 10 days of storage relative to the initial content (%) | Example 1 MES | Comp. Ex. 1 Stabilizer-free | Comp. Ex. 2 Citric acid | Comp. Ex. 3 Tartaric acid | Comp. Ex. 4 Histidine | Comp. Ex. 5 Taurine | Comp. Ex 6 Tris | Comp. Ex. 7 HEPES |
|---|---|---|---|---|---|---|---|---|
| Oxaliplatin-containing sample (storage conditions: 60° C.) | 79.4 | 85.2 | 1.6 | 30.6 | ND | 75.9 | 58.0 | 51.0 |
| HSPC-containing sample (storage conditions: 40° C.) | 83.8 | 48.5 | 97.2 | 79.8 | 94.4 | 40.9 | 86.1 | 78.1 |

ND: The target substance was not detected after storage.

The results of Table 1 reveal the following. In Example 1, the addition of MES causes little degradation of oxaliplatin (equivalent to the buffer-free Comparative Example 1), and there was also little degradation of HSPC. In contrast, in Comparative Examples 1 and 5, although there was little degradation of oxaliplatin, HSPC was greatly degraded, and the results suggested the need to add a stabilizer. In Comparative Examples 2 to 4, 6, and 7, although HSPC was stabilized, degradation of oxaliplatin was accelerated.

Production Example 1

About 60 g of a mixed lipid powder (HSPC/Chol/mPEG2000-DSPE=2/1/0.1, mol/mol) was added with stirring to 100 mL of absolute ethanol warmed to 60 to 70° C. to obtain a lipid solution. This lipid solution was added to 900 mL of a 10% sucrose solution containing 8 mg/mL oxaliplatin, which was also warmed beforehand to 60 to 70° C. The resulting mixture was stirred. A more homogeneously emulsified state was then created by using a homomixer or the like as appropriate. Subsequently, the emulsion was passed through a polycarbonate filter with a pore diameter of 0.2 μm several times to obtain a dispersion of oxaliplatin-encapsulating liposomes with a mean particle size of 100 to 200 nm.

Subsequently, unencapsulated oxaliplatin was removed by ultrafiltration using a tangential flow ultrafiltration membrane (PES, 300 kDa, 0.1 m$^2$) to obtain oxaliplatin-encapsulating liposomes (hereinafter referred to as "liposome sample No. 1").

Example 2

A high-concentration aqueous solution of MES was prepared and added to liposome sample No. 1 obtained in Production Example 1 in an amount such that the concentration of MES in the resulting formulation was 3 mM. Subsequently, the resulting mixture was adjusted to a pH of 6.0 to 6.5 with 0.1 N NaOH to obtain an MES-added oxaliplatin-encapsulating liposome aqueous dispersion.

Comparative Example 8

Liposome sample No. 1 obtained in Production Example 1 was used unmodified as an additive-free formulation.

Comparative Example 9

A high-concentration aqueous solution of Tris was prepared and added to liposome sample No. 1 in an amount such that the concentration of Tris in the resulting formulation was 3 mM. Subsequently, the resulting mixture was adjusted to a pH of 6.0 to 6.5 using a sulfuric acid solution (100-fold diluted sulfuric acid) to obtain a Tris-added formulation.

Comparative Example 10

A high-concentration aqueous solution of histidine was prepared and added to liposome sample No. 1 in an amount such that the concentration of histidine in the resulting formulation was 3 mM. Subsequently, the resulting mixture was adjusted to pH 6.0 to 6.5 using a sulfuric acid solution (100-fold diluted sulfuric acid) to obtain a histidine-added formulation.

Test Example 2 Stabilizing Effect of MES on Oxaliplatin-Containing Liposome Formulation—1

The samples obtained in Example 2 and Comparative Examples 8 to 10 were placed in vials, which were sealed tightly. The samples were then stored at 40° C. The mean particle size of the samples was determined by dynamic light scattering, and oxaliplatin and HSPC concentrations were determined by HPLC. The stabilizing effect was assessed by comparing the initial values with the values after one month of storage. Table 2 shows the results.

TABLE 2

Drug stabilizing effect of various additives (stored at 40° C.)

| | Example 2 | | | Comp. Ex. 8 | | | Comp. Ex. 9 | | | Comp. Ex. 10 | | |
|---|---|---|---|---|---|---|---|---|---|---|---|---|
| | Initial value | After one month | % | Initial value | After one month | % | Initial value | After one month | % | Initial value | After one month | % |
| Mean particle size (nm) | 147.1 | 153.3 | | 151.1 | 162.9 | | 144.6 | 162.0 | | 152.8 | 159.1 | |

TABLE 2-continued

Drug stabilizing effect of various additives (stored at 40° C.)

|  | Example 2 | | | Comp. Ex. 8 | | | Comp. Ex. 9 | | | Comp. Ex. 10 | | |
| --- | --- | --- | --- | --- | --- | --- | --- | --- | --- | --- | --- | --- |
|  | Initial value | After one month | % | Initial value | After one month | % | Initial value | After one month | % | Initial value | After one month | % |
| L-OHP concentration (mg/mL) | 0.92 | 0.88 | 95.7 | 0.96 | 0.92 | 95.8 | 0.92 | 0.82 | 89.1 | 0.94 | 9.69 | 73.4 |
| HSPC concentration (mg/mL) | 28.8 | 25.0 | 86.8 | 30.7 | 30.1 | 48.2 | 30.1 | 17.6 | 58.5 | 31.3 | 26.4 | 84.3 |
| pH | 6.3 | 6.1 |  | 5.3 | 6.2 |  | 6.2 | 3.9 |  | 6.5 | 5.4 |  |

As shown in Table 2, in Comparative Example 8 or 9, the HSPC concentration was reduced to about half of the initial value. The results confirmed degradation of liposome-forming phospholipids. In Comparative Example 10, while reduction of the HSPC concentration was suppressed, reduction of the L-OHP concentration was observed. In contrast, in Example 2, reduction of the HSPC concentration was greatly improved without affecting the L-OHP concentration.

Test Example 3 Stabilizing Effect of MES on Oxaliplatin-Containing Liposome Formulation—2

The samples obtained in Example 2 and Comparative Example 8 were placed in vials, which were sealed tightly. The samples were then stored at 2 to 8° C. The mean particle size of each sample was determined by dynamic light scattering, and the oxaliplatin and HSPC concentrations were determined by HPLC. The stabilizing effect was assessed by comparing the initial values with the values after 6 months of storage. Table 3 shows the results.

TABLE 3

Stabilizing effect of MES on the pharmaceutical preparation (5° C.)

|  | Example 2 | | | Comp. Ex. 8 | | |
| --- | --- | --- | --- | --- | --- | --- |
|  | Initial value | After 6 months | % | Initial value | After 6 months | % |
| Average particle size (nm) | 159.9 | 151.6 | 94.8 | 154.2 | 152.2 | 98.7 |
| L-OHP concentration (mg/mL) | 0.94 | 0.95 | 101.1 | 0.95 | 0.97 | 102.1 |
| HSPC concentration (mg/mL) | 31.1 | 31.0 | 99.7 | 31.1 | 24.9 | 79.9 |
| pH | 6.3 | 6.1 | 97.8 | 5.1 | 4.4 | 85.7 |

The results of Table 3 also confirmed the reduction of HSPC concentration and pH in Comparative Example 8, whereas degradation of HSPC was suppressed without affecting the L-OHP concentration in the formulation of Example 2.

Test Example 4 Relationship Between the Formulation Stabilization by MES and Formulation Properties of Oxaliplatin-Encapsulating Liposomes The samples obtained in Example 2 and Comparative Example 8 were placed in vials, which were sealed tightly. The samples were then stored at 25° C. for 4 months. After the storage, the formulations of Example 2 and Comparative Example 8 were administered to male BALB/c mice via the tail vein at an oxaliplatin dose of 4.2 mg/kg. After 6, 24, and 72 hours, blood was collected to obtain blood plasma. The Pt concentration in blood plasma was determined using an atomic absorption spectrometer. FIG. 1 shows the results.

As compared to Example 2, the formulation of Comparative Example 8 whose degradation progressed had a short circulation in blood, whereas the formulation of Example 2 maintained a high circulation in blood equivalent to the level immediately after the storage in Example 2.

Example 3

About 40 g of DSPC, about 4.8 g of cholesterol, and about 7.5 g of mPEG2000-DSPE were added with stirring to 100 mL of absolute ethanol warmed to 60 to 70° C. to obtain a lipid solution (DSPC/Chol/mPEG2000-DSPE=2/0.5/0.1, mol/mol). This lipid solution was added to 900 mL of a 10% sucrose solution containing 8 mg/mL oxaliplatin, which was also warmed beforehand to 60 to 70° C. The resulting mixture was stirred. A more homogeneously emulsified state was then created by using a homomixer or the like as appropriate. Subsequently, the emulsion was passed through a polycarbonate filter with a pore diameter of 0.2 μm several times to obtain a dispersion of oxaliplatin-encapsulating liposomes with a mean particle size of 100 to 200 nm.

Subsequently, unencapsulated oxaliplatin was removed by ultrafiltration using a tangential flow ultrafiltration membrane (PES, 300 kDa, 0.1 m$^2$) to obtain oxaliplatin-encapsulating liposomes.

A high-concentration aqueous solution of MES was prepared and added to the above-obtained liposomes in an amount such that the concentration of MES in the resulting formulation was 1 mM. Subsequently, the resulting mixture was adjusted to a pH of 6.0 to 6.5 with 0.1 N NaOH to obtain an MES-added oxaliplatin-encapsulating liposome aqueous dispersion.

Example 4

About 37 g of DPPC, about 10 g of cholesterol, and about 15 g of mPEG2000-DSPE were added with stirring to 100 mL of absolute ethanol warmed to 60 to 70° C. to obtain a lipid solution (DPPC/Chol/mPEG2000-DSPE=2/1/0.2, mol/mol). This lipid solution was added to 900 mL of a 10% sucrose solution containing 8 mg/mL oxaliplatin, which was also warmed beforehand to 60 to 70° C. The resulting mixture was stirred. A more homogeneously emulsified state was then created by using a homomixer or the like as appropriate. Subsequently, the emulsion was passed through a polycarbonate filter with a pore diameter of 0.2 µm several times to obtain a dispersion of oxaliplatin-encapsulating liposomes with a mean particle size of 100 to 200 nm.

Subsequently, unencapsulated oxaliplatin was removed by ultrafiltration using a tangential flow ultrafiltration membrane (PES, 300 kDa, 0.1 m$^2$) to obtain oxaliplatin-encapsulating liposomes.

A high-concentration aqueous solution of MES was prepared and added to the above-obtained liposomes in an amount such that the concentration of MES in the resulting formulation was 5 mM. Subsequently, the resulting mixture was adjusted to a pH of 6.0 to 6.5 with 0.1 N NaOH to obtain an MES-added oxaliplatin-encapsulating liposome aqueous dispersion.

Example 5

About 39 g of HEPC, about 15 g of cholesterol, and about 0.4 g of mPEG2000-DSPE were added with stirring to 100 mL of absolute ethanol warmed to 60 to 70° C. to obtain a lipid solution (HEPC/Chol/mPEG2000-DSPE=2/1.5/0.05, mol/mol). This lipid solution was added to 900 mL of a 10% sucrose solution containing 8 mg/mL oxaliplatin, which was also warmed beforehand to 60 to 70° C. The resulting mixture was stirred. A more homogeneously emulsified state was then created by using a homomixer or the like as appropriate. Subsequently, the emulsion was passed through a polycarbonate filter with a pore diameter of 0.2 µm several times to obtain a dispersion of oxaliplatin-encapsulating liposomes with a mean particle size of 100 to 200 nm.

Subsequently, unencapsulated oxaliplatin was removed by ultrafiltration using a tangential flow ultrafiltration membrane (PES, 300 kDa, 0.1 m$^2$) to obtain oxaliplatin-encapsulating liposomes.

A high-concentration aqueous solution of MES was prepared and added to the above-obtained liposomes in an amount such that the concentration of MES in the resulting formulation was 0.1 mM. Subsequently, the resulting mixture was adjusted to pH 6.0 to 6.5 with 0.1 N NaOH to obtain an MES-added oxaliplatin-encapsulating liposome aqueous dispersion.

The invention claimed is:

1. An oxaliplatin-encapsulating liposome aqueous dispersion comprising an external aqueous phase that contains a stabilizing amount of 2-morpholinoethanesulfonic acid, wherein the liposome comprises, as a liposome component, hydrogenated purified soybean phosphatidylcholine, wherein the oxaliplatin-encapsulating liposome aqueous dispersion has a pH of 6 to 8, wherein the dispersion comprises an internal aqueous phase that substantially contains no 2-morpholinoethanesulfonic acid, wherein said external aqueous phase does not include an amine, wherein the stabilizing amount of 2-morpholinoethanesulfonic acid has a concentration of 0.1 to 5 mM and wherein the stabilizing amount of 2-morpholinoethanesulfonic acid results in 70% or more of said hydrogenated purified soybean phosphatidylcholine remaining after 10 days when stored at 40° C.

2. The oxaliplatin-encapsulating liposome aqueous dispersion according to claim 1, wherein the dispersion has a pH of 6 to 7.

3. The oxaliplatin-encapsulating liposome aqueous dispersion according to claim 1, wherein the liposomes comprise at least one saturated phospholipid as a liposome component.

4. An oxaliplatin-encapsulating liposome aqueous dispersion, comprising an external aqueous phase that contains 2-morpholinoethanesulfonic acid, and an internal aqueous phase that substantially contains no 2-morpholinoethanesulfonic acid, wherein the liposome comprises, as a liposome component, hydrogenated purified soybean phosphatidylcholine, wherein the oxaliplatin-encapsulating liposome aqueous dispersion has a pH of 6 to 8, and wherein said oxaliplatin-encapsulating liposome aqueous dispersion is stable for at least six months when stored at 2-8° C., wherein said 2-morpholinoethanesulfonic acid is in an amount sufficient to stabilize both said oxaliplatin and said hydrogenated purified soybean phosphatidylcholine against degradation, and wherein the 2-morpholinoethanesulfonic acid has a concentration of 0.1 to 5 mM and wherein the stabilizing amount of 2-morpholinoethanesulfonic acid results in 70% or more of said hydrogenated purified soybean phosphatidylcholine remaining after 10 days when stored at 40° C.

5. The oxaliplatin-encapsulating liposome aqueous dispersion according to claim 4, wherein no precipitation, aggregation, or particle size change occurs after storage at 2-8° C. for 6 months.

6. The oxaliplatin-encapsulating liposome aqueous dispersion according to claim 4, wherein said oxaliplatin-encapsulating liposome aqueous dispersion is stable for at least 10 days at 40° C.

7. A stabilized oxaliplatin-encapsulating liposome aqueous dispersion, made by a method comprising adding 2-morpholinoethanesulfonic acid or a salt thereof to an oxaliplatin-encapsulating liposome aqueous dispersion in an amount sufficient to stabilize said oxaliplatin-encapsulating liposome aqueous dispersion, wherein the liposome comprises, as a liposome component, hydrogenated purified soybean phosphatidylcholine, wherein the oxaliplatin-encapsulating liposome aqueous dispersion has a pH of 6 to 8, wherein the dispersion comprises an internal aqueous phase that substantially contains no 2-morpholinoethanesulfonic acid, wherein the 2-morpholinoethanesulfonic acid has a concentration of 0.1 to 5 mM, and wherein at least 70% of said hydrogenated purified soybean phosphatidylcholine and said oxaliplatin remains after 10 days when stored at 40° C.

8. The stabilized oxaliplatin-encapsulating liposome aqueous dispersion according to claim 7, wherein the oxaliplatin-encapsulating liposome aqueous dispersion has a pH of 6 to 7.

9. The stabilized oxaliplatin-encapsulating liposome aqueous dispersion according to claim 7, wherein said 2-morpholinoethanesulfonic acid or a salt thereof is added to the oxaliplatin-encapsulating liposome aqueous dispersion after formation of the oxaliplatin-encapsulating liposome.

10. The stabilized oxaliplatin-encapsulating liposome aqueous dispersion according to claim 7, wherein the 2-morpholinoethanesulfonic acid or a salt thereof is added in the form of a solution or powder to the external aqueous phase.

11. A stabilized oxaliplatin-encapsulating liposome aqueous dispersion, made by a method comprising forming an oxaliplatin-encapsulating liposome aqueous dispersion with an internal aqueous phase and an external aqueous phase, and then replacing the external aqueous phase with a buffer containing 2-morpholinoethanesulfonic acid or a salt thereof in an amount sufficient to stabilize said oxaliplatin-encapsulating liposome aqueous dispersion, wherein the liposome comprises, as a liposome component, hydrogenated purified soybean phosphatidylcholine, wherein the external aqueous phase of the oxaliplatin-encapsulating liposome aqueous dispersion has a pH of 6 to 8, and wherein the internal aqueous phase contains substantially no 2-morpholinoethanesulfonic acid, wherein said 2-morpholinoethanesulfonic acid or a salt thereof is in an amount sufficient to stabilize said hydrogenated purified soybean phosphatidylcholine without degrading said oxaliplatin and to prevent the formation of precipitates or aggregates when stored at 2-8° C. for six months, wherein said oxaliplatin-encapsulating liposome has the same blood circulation time before and after storage at 25° C. for 4 months, wherein the 2-morpholinoethanesulfonic acid has a concentration of 0.1 to 5 mM and wherein the stabilizing amount of 2-morpholinoethanesulfonic acid results in at least 70% of said hydrogenated purified soybean phosphatidylcholine remaining after 10 days when stored at 40° C.

12. A stabilized oxaliplatin-encapsulating liposome aqueous dispersion, made by a method comprising:
   a) preparing a lipid solution,
   b) preparing an oxaliplatin solution,
   c) adding the lipid solution to the oxaliplatin solution to produce an oxaliplatin-encapsulating liposome aqueous dispersion, and
   d) adding 2-morpholinoethanesulfonic acid or a salt thereof to the oxaliplatin-encapsulating liposome aqueous dispersion in an amount sufficient to stabilize said oxaliplatin-encapsulating liposome aqueous dispersion, wherein the liposome comprises, as a liposome component, hydrogenated purified soybean phosphatidylcholine, wherein the oxaliplatin-encapsulating liposome aqueous dispersion has a pH of 6 to 8, and wherein the dispersion comprises an internal aqueous phase that substantially contains no 2-morpholinoethanesulfonic acid, wherein the 2-morpholinoethanesulfonic acid has a concentration of 0.1 to 5 mM, and wherein at least 70% of said hydrogenated purified soybean phosphatidylcholine remains after 10 days when stored at 40° C.

13. A composition comprising the oxaliplatin-encapsulating liposome aqueous dispersion according to claim 1, in combination with an antitumor agent.

14. The oxaliplatin-encapsulating liposome aqueous dispersion according to claim 1, wherein 75% or more of said oxaliplatin remains after 10 days when stored at 40° C.

* * * * *